(12) United States Patent
Tanino et al.

(10) Patent No.: US 8,383,844 B2
(45) Date of Patent: Feb. 26, 2013

(54) PROCESS FOR PRODUCING (±)-3A,6,6,9A-TETRAMETHYLDODE CAHYDRONAPHTHO [2,1-B]FURANS

(75) Inventors: Kenji Tanino, Wakayama (JP); Takashi Aoki, Wakayama (JP)

(73) Assignee: Kao Corporation, Tokyo (JP)

( * ) Notice: Subject to any disclaimer, the term of this patent is extended or adjusted under 35 U.S.C. 154(b) by 18 days.

(21) Appl. No.: 13/201,122

(22) PCT Filed: Jan. 21, 2010

(86) PCT No.: PCT/JP2010/051068
§ 371 (c)(1),
(2), (4) Date: Aug. 11, 2011

(87) PCT Pub. No.: WO2010/092872
PCT Pub. Date: Aug. 19, 2010

(65) Prior Publication Data
US 2011/0319642 A1    Dec. 29, 2011

(30) Foreign Application Priority Data
Feb. 16, 2009    (JP) ................................. 2009-033159

(51) Int. Cl.
*C07D 307/92* (2006.01)
(52) U.S. Cl. ..................................... 549/458
(58) Field of Classification Search ............. 549/458
See application file for complete search history.

(56) References Cited

U.S. PATENT DOCUMENTS
2009/0270639 A1    10/2009    Aoki et al.

FOREIGN PATENT DOCUMENTS
| EP | 0 165 458 | 12/1985 |
| WO | 2008 015977 | 2/2008 |
| WO | 2009 010791 | 1/2009 |

OTHER PUBLICATIONS

Barrero, et al. "Synthesis of (±)-Ambrox from (E)-Nerolidol and β-Ionone via Allylic Alcohol [2,3] Sigmatropic Rearrangement." Journal of Organic Chemistry, vol. 61, No. 6. XP 003020917. pp. 2215-2218 (1996).
International Search Report issued May 28, 2010 in PCT/JP10/51068 filed Jan. 21, 2010.

*Primary Examiner* — Bernard Dentz
(74) *Attorney, Agent, or Firm* — Oblon, Spivak, McClelland, Maier & Neustadt, L.L.P.

(57) ABSTRACT

The present invention relates to a process for producing (±)-3a,6,6,9a-tetramethyl dodecahydronaphtho[2,1-b]furans from crude (±)-3a,6,6,9a-tetramethyl dodecahydronaphtho [2,1-b]furans obtained by subjecting (±)-3a,6,6,9a-tetramethyl dodecahydronaphtho[2,1-b]furan-2(1H)-ones which are produced by cyclizing a homofarnesylic acid amide or a monocyclohomofarnesylic acid amide in the presence of an acid agent and then hydrolyzing the cyclized product, to reduction reaction and then to cyclization reaction, said process including (i) an alkali treatment step in which the crude (±)-3a,6,6,9a-tetramethyl dodecahydronaphtho[2,1-b]furans are heated in the presence of an alcohol and a metal hydroxide; and (ii) a washing treatment step in which the crude (±)-3a,6,6,9a-tetramethyl dodecahydronaphtho[2,1-b]furans are washed with an aqueous acid solution. The thus obtained (±)-3a,6,6,9a-tetramethyl dodecahydronaphtho[2,1-b]furans have a less off-odor and hardly suffer from deterioration of their smell during storage.

11 Claims, No Drawings

PROCESS FOR PRODUCING (±)-3A,6,6,9A-TETRAMETHYLDODECA HYDRONAPHTHO [2,1-B]FURANS

CROSS REFERENCE TO RELATED APPLICATION

This application is a 371 of PCT/JP10/051068, filed on Jan. 21, 2010, and claims priority to Japanese Patent Application No. 2009-033159, filed on Feb. 16, 2009.

FIELD OF THE INVENTION

The present invention relates to a process for producing (±)-3a,6,6,9a-tetramethyldodecahydronaphtho[2,1-b]furans.

BACKGROUND OF THE INVENTION

It is known that (−)-3a,6,6,9a-tetramethyl dodecahydronaphtho[2,1-b]furan represented by the following general formula (I) and optical isomers thereof (hereinafter collectively referred to as merely "(±)-ambroxan"):

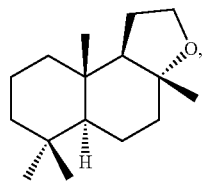

(I)

are important amber-like perfume materials having an excellent aromatizing property and an excellent aroma retention property.

The (±)-ambroxan contains a plurality of asymmetric carbons. Therefore, there are present diastereomers of the (±)-ambroxan. There is conventionally known a process for producing a mixture of the diastereomers of the (±)-ambroxan (hereinafter referred to merely as "(±)-ambroxans") represented by the following general formula (II):

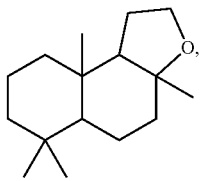

(II)

in which a homofarnesylic acid amide or a monocyclohomofarnesylic acid amide is cyclized in the presence of an acid agent and then hydrolyzed, and further the obtained hydrolyzed product is subjected to reduction reaction and cyclization reaction (refer to Patent Document 1).

Patent Document 1: Japanese Patent Application Laid-Open (kokai) No. 2008-56663

SUMMARY OF THE INVENTION

Patent Document 1 discloses an industrially advantageous process for producing (±)-ambroxans with low costs for a short period of time. However, the process has such a problem that the (±)-ambroxans (hereinafter occasionally referred to as "crude (±)-ambroxans") have amine-like off-odor immediately after production thereof.

In the course of studying a method for eliminating the amine-like off-odor, the present inventors have attempted to subject the crude (±)-ambroxans to distillation, washing treatment with an acid, etc. As a result, it has been found that although the (±)-ambroxans immediately after thus treated are almost free from the off-odor, generation of the amine-like off-odor therefrom occurs with time during storage, and the (±)-ambroxans suffer from continuous deterioration in quality of their smell. Thus, the invention of Patent Document 1 still has the problem of deterioration in quality of smell which is not readily solved by ordinary methods. In addition, the resulting (±)-ambroxans tend to be limited with respect to their applications or amounts used therein, etc.

In consequence, the present invention relates to a process for producing (±)-ambroxans which have a less off-odor and hardly suffer from deterioration of smell even during a long-term storage, by using the crude (±)-ambroxans obtained via a homofarnesylic acid amide or a monocyclohomofarnesylic acid amide as described in Patent Document 1.

DETAILED DESCRIPTION OF THE INVENTION

Thus, the present invention relates to a process for producing (±)-3a,6,6,9a-tetramethyl dodecahydronaphtho[2,1-b] furans from crude (±)-3a,6,6,9a-tetramethyl dodecahydronaphtho[2,1-b]furans (including (±)-ambroxans represented by the following general formula (II):

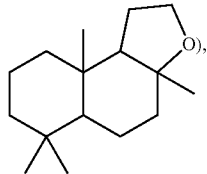

(II)

the crude (±)-3a,6,6,9a-tetramethyl dodecahydronaphtho[2,1-b]furans being obtained by subjecting (±)-3a,6,6,9a-tetramethyl dodecahydronaphtho[2,1-b]furan-2(1H)-ones (hereinafter occasionally referred to as "(±)-sclareolides") which are produced by cyclizing a homofarnesylic acid amide or a monocyclohomofarnesylic acid amide in the presence of an acid agent and then hydrolyzing the cyclized product, to reduction reaction and then to cyclization reaction, the process including:

(i) an alkali treatment step in which the crude (±)-3a,6,6,9a-tetramethyl dodecahydronaphtho[2,1-b]furans are heated in the presence of an alcohol and a metal hydroxide; and (ii) a washing treatment step in which the crude (±)-3a,6,6,9a-tetramethyl dodecahydronaphtho[2,1-b]furans are washed with an aqueous acid solution.

In accordance with the present invention, there is provided a process for producing the (±)-ambroxans (II) which have a less off-odor and hardly suffer from deterioration of their smell even during a long-term storage.

In the process for producing the (±)-ambroxans (II) according to the present invention, the crude (±)-ambroxans (II) produced according to the method described in Patent Document 1 are used. The process for producing the crude (±)-ambroxans (II) is explained below.

(Production of Homofarnesylic Acid Amide (III))

The homofarnesylic acid amide used in the present invention is a compound represented by the following general formula (III).

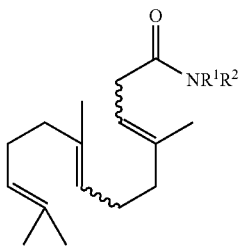

In the general formula (III), $R^1$ and $R^2$ are each independently an alkyl group having 1 to 4 carbon atoms; and wavy lines each represent a carbon-to-carbon single bond having a cis or trans structure.

The homofarnesylic acid amide (III) may be produced, for example, by reacting commercially available (±)-nerolidol and N,N-dialkylformamide diacetal represented by the following general formula (IV).

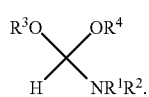

In the general formula (IV), $R^1$ and $R^2$ are the same as defined in the above general formula (III), and $R^3$ and $R^4$ are each independently an alkyl group having 1 to 4 carbon atoms.

(Production of Monocyclohomofarnesylic Acid Amide (V))

The monocyclohomofarnesylic acid amide used in the present invention is a compound represented by the following general formula (V).

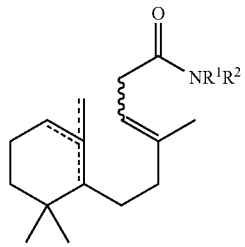

In the general formula (V), $R^1$ and $R^2$ and wavy line are the same as defined in the above general formula (III); and dotted lines represent that a carbon-to-carbon double bond is present at any of positions represented by the dotted lines.

The monocyclohomofarnesylic acid amide (V) may be produced, for example, by reacting dihydro-ionone with vinyl magnesium bromide, or by adding acetylene to the dihydro-ionone and then subjecting the resulting addition product to selective hydrogenation in the presence of a Lindlar catalyst, etc., to obtain (±)-monocyclonerolidol, followed by reacting the thus obtained (±)-monocyclonerolidol with N,N-dialkylformamide diacetal represented by the above general formula (IV) similarly to the above production of the homofarnesylic acid amide.

(Production of (±)-Sclareolides)

The (±)-sclareolides used in the present invention are compounds represented by the following general formula (VI).

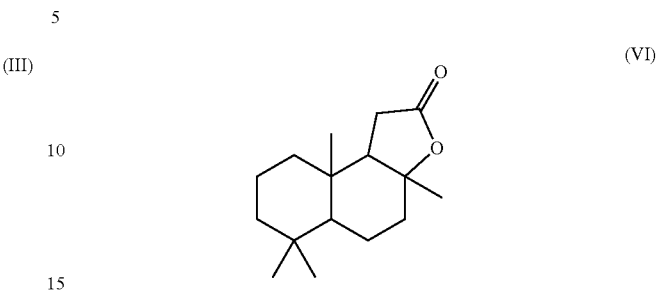

The (±)-sclareolides (VI) may be obtained by cyclizing the homofarnesylic acid amide (III) or the monocyclohomofarnesylic acid amide (V) in the presence of an acid agent and then adding water to the obtained reaction mixture to subject the cyclized product to hydrolysis.

Examples of the acid agent used in the cyclization reaction include sulfuric acid, Brønstead acids having an acidity similar to or higher than that of sulfuric acid, such as methanesulfonic acid, p-toluenesulfonic acid, chlorosulfonic acid, trifluoromethanesulfonic acid, fluorosulfonic acid, benzenesulfonic acid, trifluoroacetic acid and trichloroacetic acid, metal chlorides such as tin tetrachloride and titanium tetrachlorides, and Lewis acids such as boron trifluoride ether complexes.

(Production of Crude (±)-Ambroxans (II))

The (±)-ambroxans (II) may be produced by reducing the above (±)-sclareolides (VI) by known methods as described in DE 3240054, "Tetrahedron", Vol. 43, p. 1871, 1987, etc., and then cyclizing the reduced product. More specifically, as shown in the following chemical reaction formula (A), the (±)-sclareolides (VI) are reduced in the co-existence of a reducing agent such as aluminum lithium hydride and converted into (±)-diol isomers represented by the general formula (VII), and then the (±)-diol isomers (VII) are cyclized, for example, in the co-existence of a dehydration agent such as phosphorus oxychloride to thereby obtain the crude (±)-ambroxans (II).

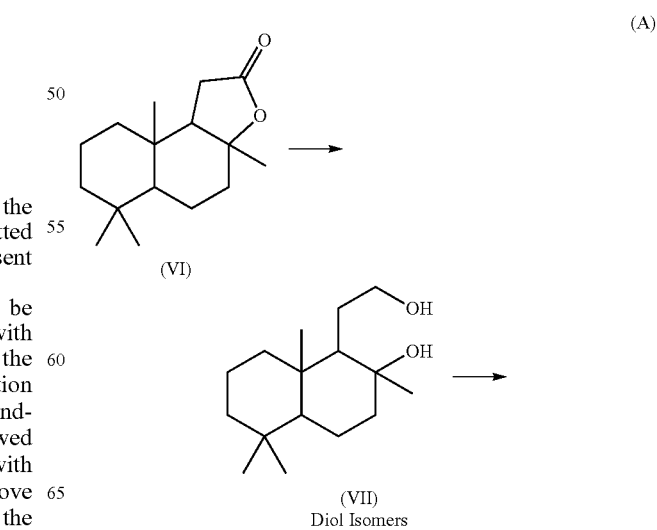

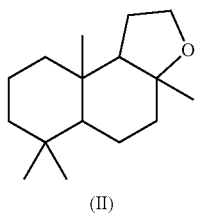

(II)

The thus obtained crude (±)-ambroxans (II) may be subjected to ordinary separation and purification methods for organic compounds such as distillation and re-crystallization. However, as described above, even when treating the crude (±)-ambroxans (II) by the ordinary separation and purification methods, the resulting purified product still tends to generate amine-like off-odor and cause deterioration in quality of smell during a long-term storage.

In accordance with the present invention, the crude (±)-ambroxans (II) obtained by the above method are subjected to at least the below-mentioned alkali treatment step (i) and washing treatment step (ii) with an aqueous acid solution (hereinafter referred to as the "acid washing treatment step (ii)"), thereby producing (±)-ambroxans (II) which have a less off-odor and hardly suffer from deterioration in smell even during a long-term storage.

[Alkali Treatment Step (i)]

In the alkali treatment step (i), the crude (±)-ambroxans (II) are heated in the presence of an alcohol and a metal hydroxide.

(Alcohol)

The alcohol used in the present invention means an organic compound having at least one hydroxyl group in a molecule thereof, and also involves those organic compounds having, in addition to the at least one hydroxyl group, one or more ether bonds or unsaturated bonds in a molecule thereof. The alcohol is preferably at least one compound selected from the group consisting of saturated or unsaturated aliphatic alcohols, alkylene glycol monoalkyl ethers, polyalkylene glycol monoalkyl ethers, glycerin, alkylene glycols and polyalkylene glycols.

The saturated or unsaturated aliphatic alcohols may be in the form of either a straight-chain alcohol or a branched alcohol. If the alcohols have a boiling point lower than the temperature at which the above treatment step is carried out, it is possible to reduce a burden for facilities such as pressure facilities. Therefore, the saturated or unsaturated aliphatic alcohols preferably have 4 or more carbon atoms, more preferably 6 or more carbon atoms, even more preferably 10 or more carbon atoms, further even more preferably 15 or more carbon atoms and further even more preferably 20 or more carbon atoms. Also, from the viewpoint of easiness in handling, the saturated or unsaturated aliphatic alcohols preferably have 50 or less carbon atoms, more preferably 30 or less carbon atoms and even more preferably 26 or less carbon atoms. Specific examples of the saturated or unsaturated aliphatic alcohols include butanol, butenol, octanol, octenol, decanol, decenol, tetradecanol, tetradecenol, eicosanol, eicosenol, tetracosanol, tetracocenol, hexacosanol and hexacocenol.

Specific examples of the alkylene glycol monoalkyl ethers include ethylene glycol monomethyl ether, ethylene glycol monoethyl ether and propylene glycol monomethyl ether. Specific examples of the polyalkylene glycol monoalkyl ethers include diethylene glycol monomethyl ether and diethylene glycol monoethyl ether. Specific examples of the alkylene glycols include ethylene glycol and propylene glycol. Specific examples of the polyalkylene glycols include diethylene glycol.

The alkylene group contained in the above alkylene glycol monoalkyl ethers or polyalkylene glycol monoalkyl ethers preferably has 2 or 3 carbon atoms and more preferably 2 carbon atoms from the viewpoint of a good availability. Also, the alkyl group contained in the above alkylene glycol monoalkyl ethers or polyalkylene glycol monoalkyl ethers preferably has 1 to 4 carbon atoms, more preferably 1 or 2 carbon atoms and even more preferably 1 carbon atom from the viewpoint of a good availability.

The alkylene group contained in the above alkylene glycols or polyalkylene glycols preferably has 2 or 3 carbon atoms and more preferably 2 carbon atoms from the viewpoint of a good availability.

Among the above-mentioned alcohols, from the viewpoint of a high off-odor reducing efficiency, preferred are polyalkylene glycols and polyalkylene glycol monoalkyl ethers, more preferred are polyalkylene glycol monoalkyl ethers, and even more preferred are diethylene glycol monomethyl ether and diethylene glycol monoethyl ether.

The amount of the alcohol used in the alkali treatment step (i) is preferably from 0.1 to 3 parts by mass per 1 part by mass of the crude (±)-ambroxans (II). The amount of the alcohol used is more preferably 0.15 part by mass or more and even more preferably 0.2 part by mass or more per 1 part by mass of the crude (±)-ambroxans (II) from the viewpoint of a high off-odor reducing efficiency, and more preferably 1.5 parts by mass or less, even more preferably 1 part by mass or less and further even more preferably 0.6 part by mass or less per 1 part by mass of the crude (±)-ambroxans (II) from the viewpoint of low production costs.

(Metal Hydroxide)

Examples of the metal hydroxide used in the alkali treatment step (i) include an alkali metal hydroxide and/or an alkali earth metal hydroxide. Specific examples of the alkali metal hydroxide include sodium hydroxide and potassium hydroxide. Specific examples of the alkali earth metal hydroxide include magnesium hydroxide and calcium hydroxide. Among these metal hydroxides, from the viewpoint of a high off-odor reducing efficiency, preferred are alkali metal hydroxides, more preferred are sodium hydroxide and potassium hydroxide, and even more preferred is sodium hydroxide.

The amount of the metal hydroxide used in the alkali treatment step (i) is preferably from 0.05 to 1 part by mass and more preferably from 0.1 to 1 part by mass per 1 part by mass of the crude (±)-ambroxans (II). From the viewpoints of easiness in handling and low production costs, the amount of the metal hydroxide used is even more preferably from 0.1 to 0.8 part by mass and further even more preferably from 0.1 to 0.5 part by mass per 1 part by mass of the crude (±)-ambroxans (II).

Meanwhile, the configuration of the metal hydroxide used is not particularly limited. For example, the metal hydroxide may be used as such or in the form of an aqueous solution. However, in the case where the metal hydroxide is added in the form of an aqueous solution, from the viewpoint of a high off-odor reducing efficiency, it is preferred that the alkali treatment step (i) be carried out by heating the reaction system to the below-mentioned temperature after or while removing water from the reaction system after completion of adding the aqueous metal hydroxide solution thereto.

The temperature used in the alkali treatment step (i) is preferably 100° C. or higher. From the viewpoint of a high off-odor reducing efficiency, the alkali treatment temperature is more preferably from 100 to 300° C., even more preferably from 150 to 300° C. and further even more preferably from 150 to 200° C.

The alkali treatment step (i) is preferably carried out while distilling off water produced from the viewpoint of a high off-odor reducing efficiency.

Meanwhile, after completion of the alkali treatment step (i), the resulting reaction product may be appropriately purified by ordinary separation and purification methods for organic compounds such as distillation.

[Acid Washing Treatment Step (ii)]

In the acid washing treatment step (ii), the crude (±)-ambroxans (II) are washed with an aqueous acid solution.

The acid used in the aqueous acid solution is not particularly limited, and as the acid, there may be appropriately used inorganic acids and organic acids. Examples of the inorganic acids include sulfuric acid, hydrochloric acid, nitric acid, phosphoric acid, boric acid and hydrofluoric acid. Examples of the organic acids include carboxylic acids such as formic acid and acetic acid, and sulfonic acids such as p-toluenesulfonic acid. Among these acids, from the viewpoint of a high off-odor reducing efficiency, preferred are inorganic acids and carboxylic acids, more preferred are sulfuric acid, hydrochloric acid, nitric acid, phosphoric acid, formic acid and acetic acid, even more preferred are sulfuric acid, hydrochloric acid and phosphoric acid, and further even more preferred is phosphoric acid.

The concentration of the acid in the aqueous acid solution is preferably from 1 to 50% by mass, more preferably from 1 to 20% by mass, even more preferably from 1 to 10% by mass and further even more preferably from 3 to 7% by mass from the viewpoint of a good handling property.

The amount of the aqueous acid solution used in the acid washing treatment step (ii) is preferably from 0.001 to 0.5 part by mass, more preferably 0.005 part by mass or more, even more preferably 0.01 part by mass or more and further even more preferably 0.02 part by mass or more in terms of the acid used therein per 1 part by mass of the crude (±)-ambroxans (II) from the viewpoint of a high off-odor reducing efficiency. Also, from the viewpoint of a good productivity and low production costs, the amount of the aqueous acid solution used is more preferably 0.2 part by mass or less, even more preferably 0.1 part by mass or less and further even more preferably 0.05 part by mass or less in terms of the acid used therein per 1 part by mass of the crude (±)-ambroxans (II).

The acid washing treatment step (ii) is preferably carried out at a temperature of from 20 to 90° C. from the viewpoints of easiness in handling and a high off-odor efficiency. The temperature of the acid washing treatment step (ii) is more preferably 30° C. or higher and even more preferably 40° C. or higher, and more preferably 70° C. or lower and even more preferably 60° C. or lower, from the viewpoint of shortened time required for separation between layers. The acid washing treatment step (ii) may be carried out in the presence or absence of a solvent capable of forming a separate layer from water such as hydrocarbons. From the viewpoint of a high off-odor reducing efficiency, the acid washing treatment step (ii) is preferably carried out in the absence of the solvent.

Meanwhile, after completion of the acid washing treatment step (ii), the obtained product may be appropriately purified by ordinary separation and purification methods for organic compounds such as distillation.

In the present invention, any of the alkali treatment step (i) and the acid washing treatment step (ii) may be carried out earlier, and any purification procedure such as removal of the solvent and distillation may be conducted between both the steps. From a high off-odor reducing efficiency, a distillative purification is preferably carried out prior to any of the alkali treatment step (i) and the acid washing treatment step (ii). In particular, a very high off-odor reducing effect is attained by conducting a purification procedure such as removal of the solvent and distillation between the alkali treatment step (i) and the acid washing treatment step (ii), and using phosphoric acid in the acid washing treatment step (ii).

EXAMPLES

In the following Production Examples, Examples and Comparative Examples, the term "%" represents "% by mass" unless otherwise specified.

(Method of Measuring Yield and Recovery Rate)

In the respective Examples, etc., the yield was determined by an internal standard quantitative determination method using a gas chromatography (hereinafter referred to merely as "GC"). However, quantitative determination of (±)-sclareolide, (±)-diol isomers and diastereomers of (±)-ambroxan was conducted by using respective calibration curves of (±)-sclareolide, (±)-diol isomers and (±)-ambroxan.

In the respective Examples, etc., the recovery rate indicates a recovery rate of (±)-ambroxans which is calculated from masses of the (±)-ambroxans as measured by the GC internal standard method before and after subjected to the respective treatments.

(Conditions of GC Analysis)

GC analyzing device: Agilent Technology 6850A
Column: DB-WAX (30 m×250 μm×0.25 μm)
Heating conditions: Oven 80° C.→6° C./min→220° C. (retained for 32 min) (total 55 min)
Carrier gas: Helium
Flow rate: 2.0 mL/min
Injection port temperature: 200° C.
Amount injected: 1 μm (split ratio: 100:1)
Detector: Flame Ionization Detector (FID)
Detector temperature: 280° C.
Internal standard: n-Tetradecane (Method for Evaluation of Off-Odor Intensity)

The off-odor intensity values of the (±)-ambroxans (II) obtained in the following Examples and Comparative Examples were determined from the results of sensory evaluation made by three expert panelists (A, B and C). The sensory evaluation for off-odor intensity was made immediately after production of the (±)-ambroxans (II) and after preserved at 25° C. for 3 weeks, according to the following ratings.

5: Very strongly sensed
4: Strongly sensed
3: Sensed
2: Slightly sensed
1: Not sensed Production Example 1

Production of Crude (±)-Ambroxans (II)

(Synthesis of Homofarnesylic Acid Amide (III))

To 663.5 g of xylene were added 736.5 g of (±)-nerolidol (3.3 mol; geometrical isomer ratio E/Z: 60/40) and 447.9 g of N,N-dimethylformamide dimethyl acetal (3.6 mol), and the resulting mixture was stirred under reflux for 24 h while distilling off methanol by-produced therefrom. After distilling off the solvent, the resulting reaction solution was subjected to distillation under reduced pressure to obtain 700 g of a mixture (homofarnesylic acid amide (III)) of four geometrical isomers of homofarnesylic acid dimethyl amide (purity: 97%; yield: 74%). As a result of analyzing the thus obtained mixture by liquid chromatography, it was confirmed that the ratios of the respective geometrical isomers were 32% for (3E,7E)-isomer, 27% for (3Z,7E)-isomer, 22% for (3E,7Z)-isomer and 19% for (3Z,7Z)-isomer.

(Synthesis of (±)-Sclareolides (VI))

A mixed solution containing 733.3 g (7.0 kmol) of concentrated sulfuric acid and 6.7 kg of dichloromethane was cooled to 0° C., and a 10% dichloromethane solution containing 666.7 g of homofarnesylic acid dimethyl amide (purity: 97%; 2.3 kmol) was added dropwise to the mixed solution over 2 h. The resulting mixture was mixed with 3.3 kg of water and then stirred at 25° C. for 50 h. After neutralizing a water layer of the resulting reaction solution with a sodium hydroxide aqueous solution, an organic layer was separated from the reaction solution, and the water layer thus separated from the organic layer was extracted with 3.3 kg of dichloromethane twice. The thus obtained organic layers were mixed together, washed with saturated brine and then dried, and further the solvent was distilled off therefrom, thereby obtaining 600.2 g of an orange solid. As a result of analyzing the thus obtained solid, it was confirmed that the orange solid contained a mixture of diastereomers of (±)-sclareolide in a total amount of 400.1 g (yield: 68%), and the diastereo-selectivity to the (±)sclareolide was 41%.

(Synthesis of (±)-Diol Isomers (VII))

Into 2.6 kg of anhydrous diethyl ether were suspended 73.3 g (1.9 mol) of aluminum lithium hydride, and the resulting suspension was cooled to 0° C. Then, a solution prepared by dissolving 523.8 g of a solid containing 238.3 g (0.9 mol) of the mixture of diastereomers of (±)-sclareolide in 2.6 kg of anhydrous diethyl ether was added dropwise to the suspension over 15 min. After completion of the dropping, the resulting mixture was further stirred under reflux for 1 h. After cooling the obtained reaction solution to room temperature, 3.9 kg of a 10% sodium hydroxide aqueous solution was added dropwise thereto, and the water layer separated from the solution was extracted with 2.6 kg of diethyl ether twice. The thus obtained organic layers were mixed together, washed with a saturated ammonium chloride aqueous solution and then dried, and further the solvent was distilled off therefrom, thereby obtaining 550.5 g of a light yellow semi-solid. As a result of analyzing the thus obtained semi-solid, it was confirmed that the semi-solid contained the mixture of diastereomers of (d)-diol isomers in a total amount of 233.1 g (yield: 96%).

(Synthesis of Crude (±)-Ambroxans (II))

A solution prepared by dissolving 510.0 g of the semi-solid containing 210.0 g (0.8 mol) of the mixture of diastereomers of (±)-diol isomers in 6.0 kg of anhydrous pyridine, was cooled to 0° C., and 156.0 g (1.0 mol) of phosphorus oxychloride was added dropwise thereto over 5 min, and the resulting mixture was further stirred for 2 h. Successively, 3.0 kg of a 10% sodium hydroxide aqueous solution was added dropwise to the resulting reaction solution at 0° C., and the water layer separated from the solution was extracted with 3.0 kg of diethyl ether twice. The thus obtained organic layers were mixed together, washed with a saturated ammonium chloride aqueous solution and then dried, and further the solvent was distilled off therefrom, thereby obtaining 450.0 g of crude (±)-ambroxans (II) in the form of an oily substance. As a result of analyzing the thus obtained oily substance, it was confirmed that the thus obtained crude (±)-ambroxans (II) contained (±)-ambroxans (II) in a total amount of 132.0 g (yield: 68%), and the diastereo-purity of (±)-ambroxans was 44%.

Example 1

(Alkali Treatment Step (i))

To 300.0 g of the crude (±)-ambroxans (II) obtained in Production Example 1 (content of (±)-ambroxans (II): 88.0 g) were added 42.2 g of solid sodium hydroxide and 84.9 g of diethylene glycol monomethyl ether, and the resulting mixture was stirred at 170° C. for 10 h while distilling off water produced. The obtained reaction solution was mixed with 147.5 g of water at 70° C., stirred and then allowed to stand to separate a water layer therefrom, thereby obtaining 256.9 g of a mixture containing 87.6 g of (±)-ambroxans (II) (recovery rate: 99.5%).

(Distillative Purification)

After completing the alkali treatment step (i), the resulting mixture was further subjected to distillation under reduced pressure (0.66 kPa) while maintaining an inside of a reaction vessel at a temperature of 152 to 224° C. to obtain 97.0 g of a mixture containing 87.4 g of the (±)-ambroxans (II) (recovery rate by distillation: 99.8%)

(Acid Washing Treatment Step (ii))

Successively, 90.0 g of the thus obtained mixture containing 81.0 g of the (±)-ambroxans (II) was mixed with 45.0 g of a 5% phosphoric acid aqueous solution, stirred at 50° C. for 30 min and then allowed to stand to separate a water layer therefrom. The similar procedure was repeated twice, thereby obtaining 89.1 g of a mixture containing 80.3 g of the (±)-ambroxans (II) (recovery rate: 99.1%).

Production conditions, recovery rates, etc., are shown in Table 1. The results of evaluation for smell of the obtained mixture are shown in Table 3.

Examples 2 to 5

The same testing and evaluating procedures as in Example 1 were repeated except for changing the alcohol used in the alkali treatment step (i) and the aqueous acid solution used in the acid washing treatment step (ii) as shown in Table 1.

Production conditions, recovery rates, etc., are shown in Table 1. The results of evaluation for smell of the obtained mixtures are shown in Table 3.

Example 6

(Alkali Treatment Step (1))

To 150.0 g of the crude (±)-ambroxans (II) obtained in Production Example 1 (content of (±)-ambroxans (II): 44.0 g) were added 21.1 g of solid sodium hydroxide and 42.5 g of diethylene glycol monomethyl ether, and the resulting mixture was stirred at 170° C. for 10 h while distilling off water produced. The obtained reaction solution was mixed with 73.8 g of water at 70° C., stirred and then allowed to stand to separate a water layer therefrom, thereby obtaining 128.5 g of a mixture containing 43.8 g of (±)-ambroxans (recovery rate: 99.5%).

(Acid Washing Treatment Step (ii))

Successively, 100.0 g of the thus obtained mixture containing 34.1 g of the (±)-ambroxans (II) was mixed with 50.0 g of a 5% phosphoric acid aqueous solution, stirred at 50° C. for 30 min and then allowed to stand to separate a water layer therefrom. The similar procedure was repeated twice, thereby obtaining 99.0 g of a mixture containing 33.8 g of the (±)-ambroxans (II) (recovery rate: 99.1%).

Production conditions, recovery rates, etc., are shown in Table 1. The results of evaluation for smell of the obtained mixture are shown in Table 3.

Example 7

(Acid Washing Treatment Step (ii))

To 250.0 g of the crude (±)-ambroxans (II) obtained in Production Example 1 (content of (±)-ambroxans (II): 73.3 g) were added 125.0 g of a 5% phosphoric acid aqueous solution. The resulting mixture was stirred at 50° C. for 30 min and then allowed to stand to separate a water layer therefrom. The similar procedure was repeated twice, thereby obtaining 247.8 g of a mixture containing 72.7 g of the (±)-ambroxans (II) (recovery rate: 99.1%).

(Distillative Purification)

The resulting mixture was further subjected to distillation under reduced pressure (0.66 kPa) while maintaining an inside of a reaction vessel at a temperature of 152 to 224° C. to obtain 102.9 g of a mixture containing 72.5 g of the (±)-ambroxans (II) (recovery rate by distillation: 99.8%).

(Alkali Treatment Step (i))

Successively, 50.0 g of the thus obtained mixture containing 35.3 g of the (±)-ambroxans (II) was mixed with 7.1 g of solid sodium hydroxide and 14.2 g of diethylene glycol monomethyl ether, and the resulting mixture was stirred at 170° C. for 10 h while distilling off water produced. The obtained reaction solution was mixed with 90.0 g of water at 70° C., stirred and then allowed to stand to separate a water layer therefrom, thereby obtaining 38.9 g of a mixture containing 35.1 g of the (±)-ambroxans (II) (recovery rate: 99.5%).

Production conditions, recovery rates, etc., are shown in Table 1. The results of evaluation for smell of the obtained mixture are shown in Table 3.

Example 8

(Acid Washing Treatment Step (ii))

To 250.0 g of the crude H-ambroxans (II) obtained in Production Example 1 (content of (±)-ambroxans (II): 73.3 g) were added 125.0 g of a 5% phosphoric acid aqueous solution. The resulting mixture was stirred at 50° C. for 30 min and then allowed to stand to separate a water layer therefrom. The similar procedure was repeated twice, thereby obtaining 247.8 g of a mixture containing 72.7 g of the (±)-ambroxans (II) (recovery rate: 99.1%).

(Alkali Treatment Step (i))

Successively, 200.0 g of the thus obtained mixture containing 58.7 g of the (±)-ambroxans (II) was mixed with 28.1 g of solid sodium hydroxide and 56.6 g of diethylene glycol monomethyl ether, and the resulting mixture was stirred at 170° C. for 10 h while distilling off water produced. The obtained reaction solution was mixed with 98.3 g of water at 70° C., stirred and then allowed to stand to separate a water layer therefrom, thereby obtaining 171.1 g of a mixture containing 58.4 g of the (±)-ambroxans (II) (recovery rate: 99.5%).

Production conditions, recovery rates, etc., are shown in Table 1. The results of evaluation for smell of the obtained mixture are shown in Table 3.

TABLE 1

| Ex. | Order of steps | Alkali treatment step (i) | | |
|---|---|---|---|---|
| | | Metal hydroxide | Alcohol | Recovery rate (%) |
| 1 | (i) → distillative purification → (ii) | NaOH | Diethylene glycol monomethyl ether | 99.5 |
| 2 | | NaOH | 2-Decyl tetradecanol | 99.5 |
| 3 | | NaOH | Diethylene glycol monomethyl ether | 99.5 |
| 4 | | NaOH | Diethylene glycol monomethyl ether | 99.5 |
| 5 | | NaOH | Diethylene glycol monomethyl ether | 99.5 |
| 6 | (i) → (ii) | NaOH | Diethylene glycol monomethyl ether | 99.5 |
| 7 | (ii) → distillative purification → (i) | NaOH | Diethylene glycol monomethyl ether | 99.5 |
| 8 | (ii) → (i) | NaOH | Diethylene glycol monomethyl ether | 99.5 |

| Ex. | Distillative purification Recovery rate (%) | Acid washing treatment step (ii) | |
|---|---|---|---|
| | | Acid (aqueous solution) | Recovery rate (%) |
| 1 | 99.8 | 5% Phosphoric acid | 99.1 |
| 2 | 99.8 | 5% Phosphoric acid | 99.1 |
| 3 | 99.8 | 5% Hydrochloric acid | 99.2 |
| 4 | 99.8 | 5% Sulfuric acid | 99.0 |
| 5 | 99.8 | 5% Acetic acid | 99.1 |
| 6 | — | 5% Phosphoric acid | 99.1 |
| 7 | 99.8 | 5% Phosphoric acid | 99.1 |
| 8 | — | 5% Phosphoric acid | 99.1 |

Comparative Example 1

The crude (±)-ambroxans (II) obtained in Production Example 1 themselves were evaluated for smell. The results are shown in Table 3.

Comparative Example 2

(Distillative Purification)

One hundred (100.0) grams of the crude (±)-ambroxans (II) obtained in Production Example 1 (content of (±)-ambroxans (II): 29.3 g) were subjected to distillation under reduced pressure (0.66 kPa) while maintaining an inside of a reaction vessel at a temperature of 152 to 224° C. to obtain 41.5 g of a mixture containing 29.3 g of (±)-ambroxans (II) (recovery rate by distillation: 99.8%).

Production conditions, recovery rates, etc., are shown in Table 2. The results of evaluation for smell of the obtained mixture are shown in Table 3.

Comparative Example 3

The same testing and evaluating procedures as in Example 1 were repeated except for using tetraethylene glycol dimethyl ether (ether) in place of the diethylene glycol monomethyl ether (alcohol) used in the alkali treatment step (i).

Production conditions, recovery rates, etc., are shown in Table 2. The results of evaluation for smell of the obtained mixture are shown in Table 3.

Comparative Example 4

(Alkali Treatment Step (i))

To 150.0 g of the crude (±)-ambroxans (II) obtained in Production Example 1 (content of (±)-ambroxans (II): 44.0 g) were added 21.1 g of solid sodium hydroxide and 42.5 g of diethylene glycol monomethyl ether, and the resulting mixture was stirred at 170° C. for 10 h while distilling off water produced. The obtained reaction solution was mixed with 73.8 g of water at 70° C., stirred and then allowed to stand to separate a water layer therefrom, thereby obtaining 128.4 g of a mixture containing 43.8 g of (±)-ambroxans (II) (recovery rate: 99.5%).

Production conditions, recovery rates, etc., are shown in Table 2. The results of evaluation for smell of the obtained mixture are shown in Table 3.

Comparative Example 5

(Acid Washing Treatment Step (ii))

To 50.0 g of the crude (±)-ambroxans (II) obtained in Production Example 1 (content of (±)-ambroxans (II): 14.7 g) were added 25.0 g of a 5% phosphoric acid aqueous solution. The resulting mixture was stirred at 50° C. for 30 min and then allowed to stand to separate a water layer therefrom. The similar procedure was continuously repeated twice, thereby obtaining 49.0 g of a mixture containing 14.5 g of the (±)-ambroxans (II) (recovery rate: 99.1%).

Production conditions, recovery rates, etc., are shown in Table 2. The results of evaluation for smell of the obtained mixture are shown in Table 3.

TABLE 2

| | Steps | | | |
|---|---|---|---|---|
| | | Alkali treatment step (i) | | |
| Comp. Ex. | Order of steps | Metal hydroxide | Co-existing substance | Recovery rate (%) |
| 1 | — | — | — | — |
| 2 | Only distillative purification | — | — | — |
| 3 | (i) → distillative purification → (ii) | NaOH | Diethylene glycol dimethyl ether | 99.4 |
| 4 | Only (i) | NaOH | Diethylene glycol monomethyl ether | 99.5 |
| 5 | Only (ii) | — | — | — |

| | Steps | | |
|---|---|---|---|
| | Distillative | Acid washing treatment step (ii) | |
| Comp. Ex. | purification Recovery rate (%) | Acid (aqueous solution) | Recovery rate (%) |
| 1 | — | — | — |
| 2 | 99.8 | — | — |
| 3 | 99.8 | 5% Phosphoric acid | 99.1 |
| 4 | — | — | — |
| 5 | — | 5% Phosphoric acid | 99.1 |

TABLE 3

| | | Results of sensory evaluation | | | | | | | |
|---|---|---|---|---|---|---|---|---|---|
| | | Immediately after production | | | | After preserved at 25° C. for 3 weeks | | | |
| | | A | B | C | Average | A | B | C | Average |
| Ex. | 1 | 1 | 1 | 1 | 1.0 | 1 | 1 | 1 | 1.0 |
| | 2 | 1 | 1 | 1 | 1.0 | 1 | 1 | 1 | 1.0 |
| | 3 | 1 | 2 | 1 | 1.3 | 2 | 2 | 2 | 2.0 |
| | 4 | 2 | 2 | 1 | 1.7 | 2 | 2 | 2 | 2.0 |
| | 5 | 2 | 2 | 2 | 2.0 | 2 | 3 | 2 | 2.3 |
| | 6 | 1 | 1 | 2 | 1.3 | 2 | 2 | 2 | 2.0 |
| | 7 | 1 | 1 | 1 | 1.0 | 1 | 1 | 1 | 1.0 |
| | 8 | 1 | 1 | 2 | 1.3 | 2 | 2 | 2 | 2.0 |
| Comp. Ex. | 1 | 4 | 4 | 4 | 4.0 | 5 | 5 | 5 | 5.0 |
| | 2 | 4 | 4 | 4 | 4.0 | 5 | 5 | 5 | 5.0 |
| | 3 | 2 | 3 | 2 | 2.3 | 4 | 4 | 4 | 4.0 |
| | 4 | 4 | 4 | 4 | 4.0 | 4 | 4 | 5 | 4.3 |
| | 5 | 2 | 3 | 3 | 2.7 | 4 | 4 | 4 | 4.0 |

From Table 3, it was confirmed that in any of the evaluation results immediately after production of the (±)-ambroxans (II) and after preserving the (±)-ambroxans (II) for 3 weeks, the (±)-ambroxans (II) produced in Examples 1 to 8 had a considerably reduced amine-like off-odor as compared to those produced in Comparative Examples 1 to 5, in particular, that the (±)-ambroxans (II) produced in Examples 1, 2 and 7 had no amine-like off-odor both immediately after production of the (±)-ambroxans (II) and after preserving the (±)-ambroxans (II) for 3 weeks.

Therefore, according to the production process of the present invention, when the crude (±)-ambroxans (II) produced via a homofarnesylic acid amide or a monocyclohomofarnesylic acid amide are subjected to the alkali treatment and the acid washing treatment, it is possible to produce (±)-3a,6,6,9a-tetramethyl dodecahydronaphtho[2,1-b]furans ((±)-ambroxans (II)) which have a less amine-like off-odor and hardly suffer from deterioration in smell during storage.

Industrial Applicability

The (d)-3a,6,6,9a-tetramethyl dodecahydronaphtho[2,1-b]furans obtained according to the present invention have a less amine-like off-odor and hardly suffer from deterioration in smell during storage, and are, therefore, useful as a raw material for amber-like perfumes having an excellent aromatizing property and an excellent aroma retention property.

The invention claimed is:

1. A process, comprising:
    (a) producing (±)-3a,6,6,9a-tetramethyl-dodecahydronaphtho[2,1-b]furan-2(1H)-ones by cyclizing a homofarnesylic acid amide or a monocyclohomofarnesylic acid amide in the presence of an acid agent, then hydrolyzing the cyclized product;
    (b) producing a crude (±)-3a,6,6,9a-tetramethyl-dodecahydronaphtho[2,1-b]furan by subjecting the (±)-3a,6,6,9a-tetramethyl dodecahydronaphtho[2,1-b]furan-2(1H)-ones to reduction reaction and then to a cyclization reaction;
    (c) treating the crude (±)-3a,6,6,9a-tetramethyl dodecahydronaphtho[2,1-b]furan by heating in the presence of an alcohol and a metal hydroxide; and
    (d) washing the treated (±)-3a,6,6,9a-tetramethyl dodecahydronaphtho[2,1-b]furan with an aqueous acid solution.

2. The process according to claim 1, wherein said (c) treating is carried out at a temperature of from 100 to 300° C.

3. The process according to claim 1, wherein the alcohol present during said (c) treating comprises at least one alcohol selected from the group consisting of a saturated or unsaturated aliphatic alcohol, an alkylene glycol monoalkyl ether, a polyalkylene glycol monoalkyl ether, glycerin, an alkylene glycol and a polyalkylene glycol.

4. The process according to any one of claims 1, wherein the metal hydroxide present during said (c) treating comprises at least one of an alkali metal hydroxide and an alkali earth metal hydroxide.

5. The process according to any one of claims 1, wherein an acid present in the aqueous acid solution comprises sulfuric acid, hydrochloric acid, nitric acid, phosphoric acid, formic acid or acetic acid.

6. The process according to claim 2, wherein the alcohol present during said (c) treating comprises at least one alcohol selected from the group consisting of a saturated or unsaturated aliphatic alcohol, an alkylene glycol monoalkyl ether, a polyalkylene glycol monoalkyl ether, glycerin, an alkylene glycol and a polyalkylene glycol.

7. The process according to claim 2, wherein the metal hydroxide present during said (c) treating comprises at least one of an alkali metal hydroxide and an alkali earth metal hydroxide.

8. The process according to claim 3, wherein the metal hydroxide present during said (c) treating comprises at least one of an alkali metal hydroxide and an alkali earth metal hydroxide.

9. The process according to claim 2, wherein an acid present in the aqueous acid solution comprises sulfuric acid, hydrochloric acid, nitric acid, phosphoric acid, formic acid or acetic acid.

10. The process according to claim 3, wherein an acid present in the aqueous acid solution comprises sulfuric acid, hydrochloric acid, nitric acid, phosphoric acid, formic acid or acetic acid.

11. The process according to claim 4, wherein an acid present in the aqueous acid solution comprises sulfuric acid, hydrochloric acid, nitric acid, phosphoric acid, formic acid or acetic acid.

* * * * *